United States Patent [19]
Oka et al.

[11] Patent Number: 5,679,657
[45] Date of Patent: Oct. 21, 1997

[54] LOW MOLECULAR WEIGHT ACETYLHYALURONATE, SKIN-SOFTENING COMPOSITION, METHOD OF MANUFACTURING THE SAME, AND METHOD OF PURIFYING THE SAME

[75] Inventors: Takashi Oka; Toshio Yanaki; Michihiro Yamaguchi, all of Yokohama, Japan

[73] Assignee: Shiseido Co., Ltd., Tokyo, Japan

[21] Appl. No.: 624,634

[22] PCT Filed: Aug. 11, 1995

[86] PCT No.: PCT/JP95/01613

§ 371 Date: Aug. 2, 1996

§ 102(e) Date: Aug. 2, 1996

[87] PCT Pub. No.: WO96/05233

PCT Pub. Date: Feb. 22, 1996

[30] Foreign Application Priority Data

Aug. 11, 1994 [JP] Japan ................................ 6-210611
Jun. 29, 1995 [JP] Japan ................................ 7-186156

[51] Int. Cl.$^6$ ................ A61K 31/715; C07H 5/06; C07H 13/04; C07H 1/00
[52] U.S. Cl. ................ 514/54; 514/53; 536/55.2; 536/55.3; 536/115; 536/116; 536/119; 536/124; 536/127
[58] Field of Search ............ 514/54, 53; 536/55.2, 536/55.3, 115, 119, 116, 124, 127

[56] References Cited

FOREIGN PATENT DOCUMENTS 3-143540  6/1991  Japan .
6-9707    1/1994  Japan .

*Primary Examiner*—John Kight
*Assistant Examiner*—Everett White
*Attorney, Agent, or Firm*—Ronald R. Snider

[57] ABSTRACT

Low molecular weight acetylhyaluronate has the following characteristics:

intrinsic viscosity: 50 to 200 cm$^3$/g substitution degree of acetyl group: 2.6 to 3.6 (excluding N-acetyl group)

A skin-softening composition is mainly composed of this low molecular weight acetylhyaluronate. It can exhibit excellent skin-softening effect and moisturizing effect, while appropriately suppressing the thread-forming ability inherent in hyaluronic acid. A method of manufacturing acetylhyaluronate comprises the steps of suspending hyaluronic acid powder in an acetic anhydride solvent and then adding concentrated sulfuric acid thereto to effect acetylation. A method of purifying acetylhyaluronate comprises the steps of adding raw acetylhyaluronate to an aqueous acetone solution, adding and dissolving sodium lactate therein, and then adding highly concentrated acetone thereto to precipitate highly pure acetylhyaluronate. Acetylhyaluronate having highly purity can be obtained inexpensively.

9 Claims, 4 Drawing Sheets

LOW MOLECULAR WEIGHT ACETYLHYALURONATE, SKIN-SOFTENING COMPOSITION, METHOD OF MANUFACTURING THE SAME, AND METHOD OF PURIFYING THE SAME

[FIELD OF THE INVENTION]

The present invention relates to a low molecular weight acetylhyaluronate, a skin-softening composition, a method of manufacturing the same, and a method of purifying the same. In particular, it relates to improvement in acetylhyaluronate in which acetyl group is bonded to alcoholic hydroxyl group thereof with a high rate.

[BACKGROUND OF THE INVENTION]

Hyaluronic acid is a high molecular weight material derived from organisms and has specific physical characteristics such as high viscous property, viscoelasticity, and thread-forming ability, while having high biocompatibility. Accordingly, it is expected to be applied to various fields.

In particular, it should be a notable physical characteristic that hyaluronic acid has a very high moisturizing effect. Accordingly, it is used as a humectant in various external preparations for skin. Further, it is expected to be used as a thickener in organic solvent systems, various emulsification stabilizers in oily bases, a coating enforcement for liposomes, an embedded base for organisms, a capsule base, or the like.

However, since hyaluronic acid has various kinds of specific physical characteristics mentioned above, due to a part of its characteristics, it may deteriorate the usability of a product when a large amount of it is added thereto.

Also, since it is highly water-soluble, hyalucronic acid cannot be used as a humectant in organic solvent systems or oily bases.

[DISCLOSURE OF THE INVENTION]

In view of the foregoing problems of the prior art, the first object of the present invention is to provide inexpensive methods for manufacturing and purifying acetylhyaluronate which has various kinds of specific physical characteristics while maintaining the functions inherent in hyaluronic acid.

The second object of the present invention is to provide low molecular weight acetylhyaluronate which can exhibit an excellent skin-softening effect while improving shortcomings in hyaluronic acid such as thread-forming ability.

As a result of diligent studies conducted by the inventors in order to attain the above-mentioned objects, it has been found that acetylhyaluronate can be inexpensively manufactured when hyaluronic acid is reacted in the presence of acetic anhydride and concentrated sulfuric acid and that a specific kind of acetylhyaluronate having specific limiting viscosity and substitutional number of acetyl group, namely, specific molecular weight and hydrophobic property, can be remarkably improved in terms of thread-forming ability and can exhibit a high level of skin-softening effect. Thus, the present invention has been accomplished.

Namely, low molecular weight acetylhyaluronate in accordance with the present invention is characterized by the following characteristics:

intrinsic viscosity: 50 to 200 cm$^3$/g substitution degree of acetyl group: 2.6 to 3.6 (excluding N-acetyl group)

Here, in the present invention, the intrinsic viscosity refers to that measured in phosphate buffer solution of pH 7.4 at 25° C.

The a skin-softening composition in accordance with the present invention is mainly composed of low molecular weight hyaluronic acid.

The method of manufacturing acetylhyaluronate in accordance with the present invention is characterized by comprising the steps of suspending hyaluronic acid powder in an acetic anhydride solvent and then adding concentrated sulfuric acid thereto to effect acetylation, thereby yielding acetylhyaluronate.

In the above-mentioned method, acetic acid may preferably be mixed into the acetic anhydride solvent with a mixing ratio of acetic acid:acetic anhydride at 1:4 to 1:1. In this case, highly acetylhyaluronate having a high acetylation rate can be obtained.

Also, acetic acid may preferably be mixed into the acetic anhydride solvent with a mixing ratio of acetic acid:acetic anhydride at 2:1 to 4:1. In this case, acetylation advances mildly, whereby minute control of the acetylation rate can be easily effected.

Preferably, an amount of concentrated sulfuric acid added is 2 to 7% by volume with respect to the solvent.

The method of purifying acetylhyaluroate in accordance with the present invention is characterized by comprising the steps of adding raw acetylhyaluronate to an aqueous acetone solution, adding and dissolving sodium lactate therein, and then adding highly concentrated acetone thereto to attain acetylhyaluronate having highly purity.

Preferably, an amount of sodium lactate added is 1 to 3% by weight with respect to the aqueous acetone solution.

Also, preferably, the above-mentioned purifying method is applied to raw acetylhyaluronate obtained by the above-mentioned manufacturing method.

In the following, the constituents of the present invention will be explained in further detail.

Low molecular weight acetylhyaluronate in accordance with the present invention has a structure shown in the following structural formula 1:

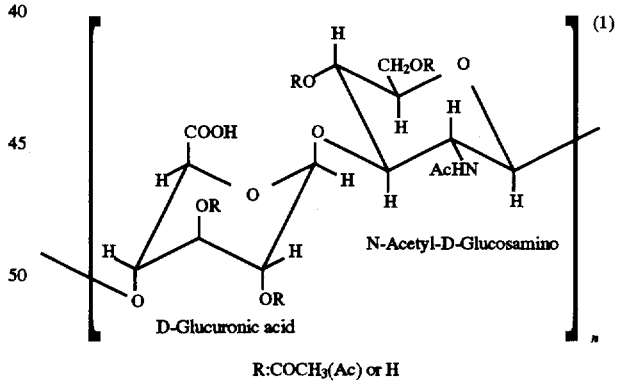

When low molecular weight acetylhyaluronate in accordance with the present invention is used for a skin-softening composition, it is necessary for the molecular weight thereof, as expressed by its intrinsic viscosity, to be within the range of 50 to 200 cm$^3$/g as mentioned above. Here, the intrinsic viscosity is used since it is difficult for the molecular weight of acetylhyaluronate to be directly indicated.

When the intrinsic viscosity is 50 cm$^3$/g or less, it becomes harder to obtain the skin-softening effect resulting from acetylhyaluronate. On the other hand, when the intrinsic viscosity is 200 cm$^3$/g or more, unfavorable physical characteristics such as thread-forming ability cannot be fully suppressed even by acetylation.

The degree of acetylation, expressed by the substitution degree of acetyl group, is preferably not less than 2.6 but not greater than 3.6. Here, while hyaluronic acid has four alcoholic hydroxyl groups in its repeating unit as shown in the above-mentioned structural formula 1, the substitution degree of acetyl group indicates how many of these groups are substituted by acetyl group.

When the substitution degree of acetyl group is less than 2.6, the hydrophobic characteristic tends to be insufficiently provided. When the substitution degree of acetyl group exceeds 3.6, on the other hand, the hydrophilic characteristic may be lowered or usability may be deteriorated, for example.

Japanese Unexamined Patent Publication No. 3-143540, for example, discloses an emulsification stabilizer in which an acyl group such as acetyl group is introduced in the repeating unit of hyaluronic acid. However, this hyaluronic acid. However, this hyaluronic acid derivative has a very low modification ratio with acyl group/N-acetyl group ratio of less than a few tenths. Namely, only one acyl group is introduced in every several or several ten repeating units. Accordingly, effects of the present invention cannot be obtained thereby. Also, when used as an emulsifier, the function for emulsifier cannot be practically attained unless highly oily acyl group such as palmitoyl group is introduced therein. Further, since pyridine system is used, hyaluronic acid may be remarkably decomposed when its modification ratio is intended to be increased, thereby losing the inherent function of hyaluronic acid.

Also, Japanese Unexamined Patent Publication Hei No. 6-9707 discloses a method of manufacturing highly acetyl-hyaluronate. Though this method is excellent in that a high acetylation ratio can be obtained under a mild condition, expensive agents are used therein. Accordingly, there has been a demand for easier and less expensive methods for manufacturing acetylhyaluronate. Also, this is rather directed to high molecular weight acetylhyaluronate and not suggest that low molecular weight acetylhyaluronate has a high skin-softening effect as in the case of the present invention.

Preferably, acetylhyaluronate in accordance with the present invention is made in the following manner.

Namely, hyaluronic acid powder is suspended in an acetic anhydride solvent and then concentrated sulfuric acid is added thereto to effect acetylation.

At this time, acetic acid is preferably mixed into the acetic anhydride solvent with a mixing ratio of acetic acid:acetic anhydride at 1:4 to 1:1. In this case, low molecular weight acetylhyaluronate having a high acetylation rate can be obtained.

Also, when the mixing ratio of acetic acid:acetic anhydride is 2:1 to 4:1, the degree of acetyl group substitution can be finely controlled.

Preferably, an amount of concentrated sulfuric acid added is 2 to 7% by volume with respect to the solvent.

On the other hand, acetylhyaluronate in accordance with the present invention can be purified when raw acetylhyaluronate is added to an aqueous acetone solution, sodium lactate is added and dissolved therein, and then acetone is added thereto, thereby yielding acetylhyaluronate having high purity.

Here, 1 to 3% by weight of sodium lactate with respect to the aqueous acetone solution is added, preferably.

In the present invention, "hyaluronic acid" refers to hyaluronic acid and its salts and may have various molecular weights.

In the method of manufacturing acetylhyaluronate in accordance with the present invention, upon enzymatic treatment using such as hyaluronidase, hyaluronic acid having a wide range of acetylation rate with a molecular weight from oligohyaluronic acid to 10,000 kd or more can be obtained. Also, the modification rate can be altered by changing the reaction time of esterification.

In the method of purifying acetylhyaluronate in accordance with the present invention, sodium lactate is added in order to deposit acetylhyaluronate due to its salting out effect. Namely, sodium lactate is dissolved beforehand, for example, in 80% aqueous acetone solution which can dissolve acetylhyaluronate. When the acetone content is increased until 92% by addition of acetone, acetylhyaluronate is deposited as a gel-like precipitate. As a salt used for this salting out process, sodium acetate, tri-sodium citrate, sodium glutamate, sodium chloride, sodium pyrrolidonecarbonate, sodium tartrate, glycine, magnesium sulfate, and potassium chloride have been studied. While sodium acetate has exhibited some salting out effect, no substantial effects have been recognized in the others. On the other hand, sodium lactate has exhibited quite favorable effects.

The purifying method in accordance with the present invention utilizes the original solvent-solubility of acetylhyaluronate made by the above-mentioned manufacturing method. Acetylhyaluronate having high purity can be obtained with a favorable yield in particular when the manufacturing method and purifying method in accordance with the present invention are combined together.

With regard to the amount of sodium lactate added, while the recovery of acetylhyaluronate can be improved when the amount of added sodium lactate is increased, the subsequent step for removing sodium lactate by ethanol may become difficult thereby. Accordingly, the minimum amount of sodium lactate added was studied in order that the recovery of acetylhyaluronate becomes high as well as the remaining rate of sodium lactate is low by control of the amount of acetone added when acetylhyaluronate was deposited as a gel-like precipitate upon increase in acetone concentration. As a result, it has been determined that an amount of sodium lactate is 1 to 3% by weight with respect to the aqueous acetone solution.

As explained in the foregoing, in the method of manufacturing acetylhyaluronate in accordance with the present invention, acetylhyaluronate can be manufactured inexpensively.

Also, in the method of purifying acetylhyaluronate in accordance with the present invention, purifying of acetylhyaluronate can be efficiently advanced.

Thus obtained acetylhyaluronate may have remarkably different physical characteristics according to its viscosity, modification ratio, and the like. For example, when it has a high viscosity and a medium degree of modification, a stable gel may be formed upon addition of a small amount of an organic solvent thereto so as to be expected to apply as a base for cosmetic or for drag delivery systems.

Also, when it has a high viscosity and a high acetylation or it has a low viscosity, it can be dissolved in an organic solvent having a considerable concentration, and it can be easily blended in emulsified lotion, for example. When it is blended in emulsified lotion or the like, various effects such as improvement in smoothness during use can be exhibited. Also, when its lipo-solubility is increased upon acetylation, its affinity to a stratum corneum whose surface is a lipid membrane can be increased, thereby improving its biocompatibility.

Further, highly acetylhyaluronate in accordance with the present invention has an advantageous effect that thread-forming ability, which is a shortcoming of hyaluronic acid as well, can be remarkably reduced when blended in cosmetics or the like.

In the a skin-softening composition of the present invention, in addition to the above-mentioned constituents, various ingredients which have been conventionally blended in external preparations for skin can be blended. Examples of such ingredients include oil contents such as liquid paraffin, squalane, lanolin derivatives, higher alcohols, various ester oils, silicone oil, polyalkyleneglycol polyether and other carboxylic acids, oligoester compounds, and terpene type hydrocarbon oils; surface active agents; ultraviolet absorbents; ultraviolet scattering agents; resins such as acrylic resin, silicone resin, and polyvinylpyrrolidone; proteins or protein decomposition products such as soybean protein, gelatin, collagen, silk fibroin, and elastin; antiseptics such as ethyl paraben and butyl paraben; activating agents such as biotin and pantothenic acid derivatives; diluents such as ethanol, isopropanol, tetrachlorodifluoroethane, and toluene; viscosity enhancing agents such as carboxyvinylpolymers; chelating agents; antioxidants; humectants; medicaments; perfumes; and coloring agents.

[BEST MODE FOR CARRYING OUT THE INVENTION]

Figure 1:
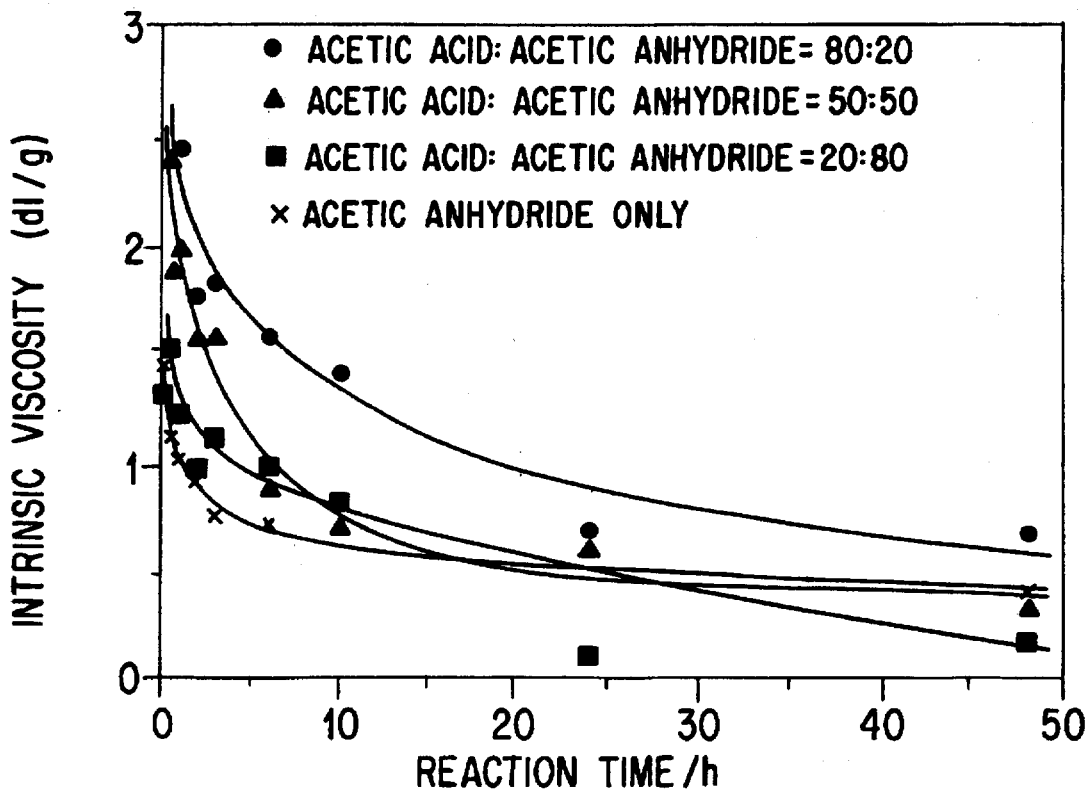
FIG. 1 is an explanatory chart showing the relationship between the reaction time of acetylation and the intrinsic viscosity when the solvent ratio of acetic acid to acetic anhydride is changed in the method of manufacturing acetylhyaluronate in accordance with the present invention.

In the following, the present invention will be explained with reference to its examples. However, the present invention should not be limited to the following examples.

MANUFACTURING EXAMPLE 1

Method of Manufacturing Acetylhyaluronate

Commercially available guaranteed acetic acid (20 ml) and acetic anhydride (80 ml) were introduced into a conical glass flask having a capacity of 300 ml and fine powder of Biohyalo-12 (hyaluronic acid having a molecular weight of about 1,200 kd, manufactured by Shiseido Co., Ltd.) (6 g) was gradually added thereto while being stirred. Then, concentrated sulfuric acid (4 ml) was gradually added to the mixture and stirred for one hour at room temperature so as to effect acetylation reaction. The reaction solution became a viscous white solution. When the degree of substitution of thus obtained acetylhyaluronate was measured, it was found to be a tri-substituted product. The yield calculated on the basis thereof was 88.8%.

PREPARATION EXAMPLE 1

Method of Purifying Acetylhyaluronate

Into a glass beaker having a capacity of 3 L, pitied water (2 L) was introduced and the above-mentioned reaction solution was gradually added thereto like a string. The resulting precipitate of acetylhyaluronate was collected and washed twice similarly with purified water (2 L). This precipitate was transferred to a glass beaker having a capacity of 1 L and then 80% (v/v) aqueous acetone solution (250 ml) and 50% aqueous sodium lactate solution (9 g) were added thereto, so as to completely dissolve the precipitate while being stirred. Subsequently, acetone (400 ml) was gradually added to the solution, thereby depositing the gel-like precipitate of acetylhyaluronate again. After this precipitate had been collected, it was subjected to two sets of washing with ethanol (100 ml) by using a homogenizer at 10,000 rpm for 10 minutes. Then, the precipitate was collected by filtration under reduced pressure and dried under vacuum, thereby yielding a white powder of acetylhyaluronate.

As a result, 6.5 g of acetylhyaluronate (yield of 82.5%) was obtained. While 0.2% of lactic add with respect to this product was remaining, neither acetic acid nor sulfuric acid was detected.

Also, this product was soluble in 90% ethanol.
Influence of Reaction Solvent Ratio Next, the inventors studied the relationship between the reaction time of acetylation and the intrinsic viscosity or substitution degree of acetyl group of acetylhyaluronate generated, when the ratio of acetic acid to acetic anhydride is changed under basically the same condition as that of the above-mentioned Manufacturing Example 1.

Figure 2:
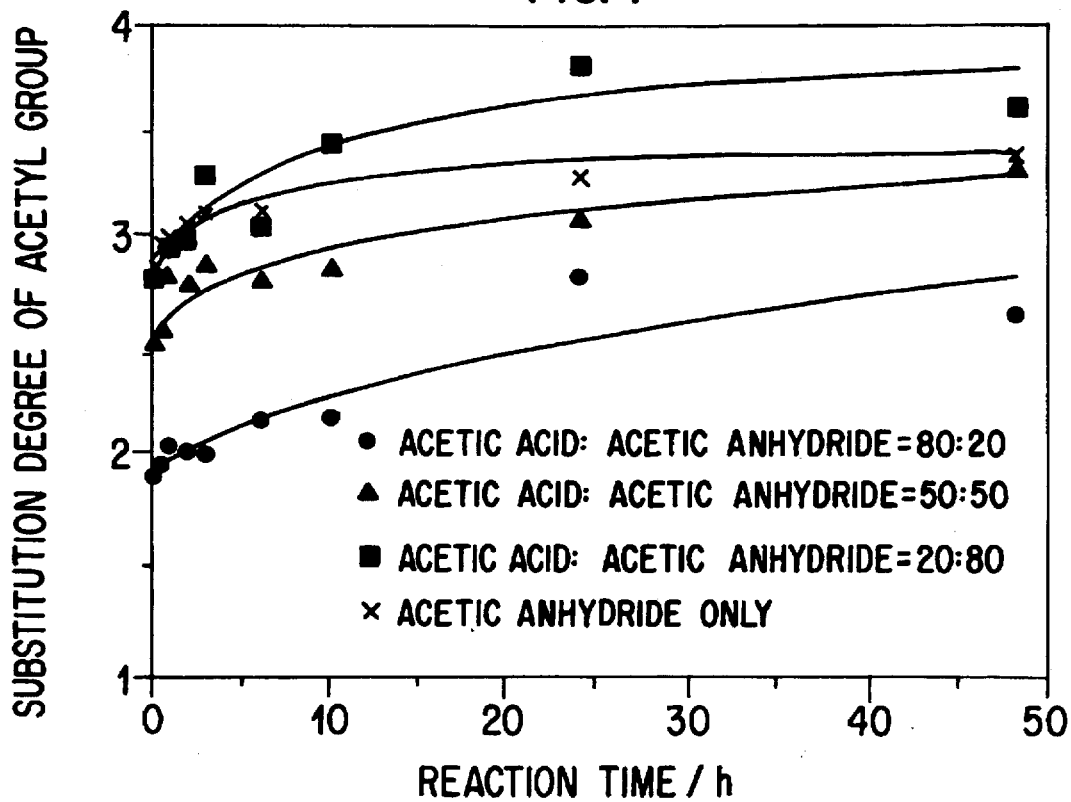
FIG. 2 is an explanatory chart showing the relationship between the reaction time of acetylation and the substitution degree of acetyl group when the solvent ratio of acetic acid to acetic anhydride is changed in the method of manufacturing acetylhyaluronate in accordance with the present invention.

FIG. 1 shows the relationship between the reaction time of acetylation and the intrinsic viscosity and FIG. 2 shows that between the reaction time of acetylation and the substitution degree of acetyl group.

As can be seen from these charts, the substitution degree of acetyl group drastically increases within several hours or, in particular, within an hour after the reaction is started. On the other hand, the viscosity drastically decreases until about 5 to 10 hours after the reaction is started. Accordingly, preferably, the reaction time is kept at one hour or less in order to obtain acetylhyaluronate having a high viscosity, while it is extended to the range of 5 to 10 hours in order to obtain acetylhyaluronate having a low viscosity.

With respect to the solvent ratio, on the other hand, the advance of acetylation is improved when acetic acid is somewhat added thereto as compared with the case where acetic anhydride is used alone. In particular, when the ratio of acetic acid:acetic anhydride is about 1:4, acetylation advances more effectively. Even when the ratio of acetic acid:acetic anhydride is about 1:1, acetylation advances and viscosity decreases to substantially the same extent as that in the case where acetic anhydride is used alone.

Accordingly, the solvent ratio of acetic acid to acetic anhydride for effectively advancing acetylation is preferably at 1:4 to 1:1 in particular. In order to adjust the substitution degree of acetyl group to a low level, on the other hand, the ratio of acetic acid:acetic anhydride is rather held at about 1:2 to 4:1, whereby the fluctuation in the substitution degree of acetyl group becomes small over time and its adjustment becomes easy.

Change in Reaction Catalyst Amount

Figure 3:
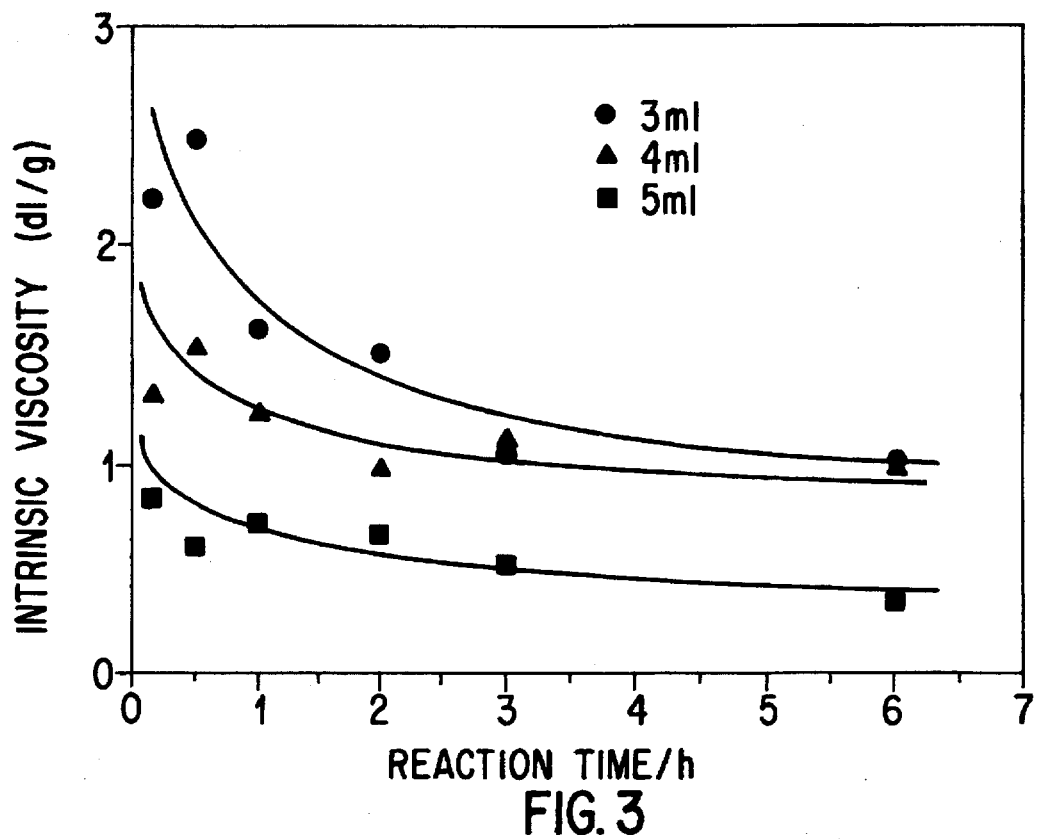
FIG. 3 is an explanatory chart showing the relationship between the reaction time of acetylation and the intrinsic viscosity when the amount of reaction catalyst (concentrated sulfuric acid) is changed in the method of manufacturing acetylhyaluronate in accordance with the present invention.
Figure 4:
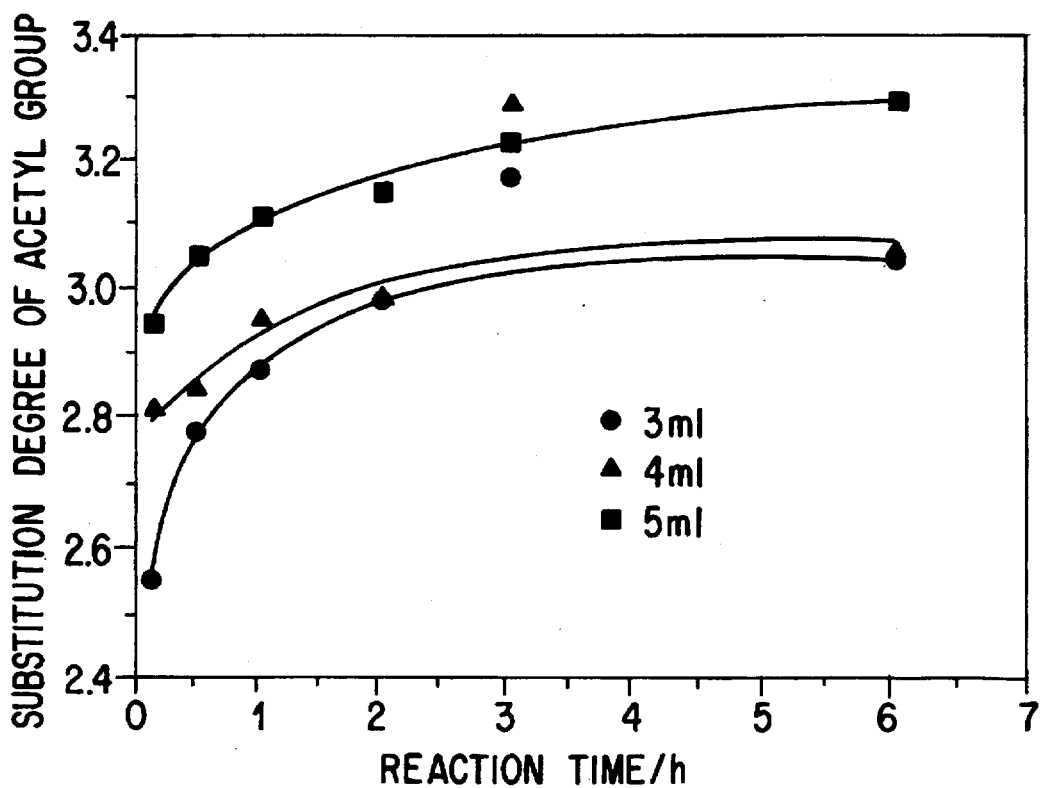
FIG. 4 is an explanatory chart showing the relationship between the reaction time of acetylation and the substitution degree of acetyl group when the amount of reaction catalyst (concentrated sulfuric acid) is changed in the method of manufacturing acetylhyaluronate in accordance with the present invention.

While sulfuric acid becomes a catalyst for advancing acetylation of hyaluronic acid, the amount of this reaction catalyst also influences the intrinsic viscosity and substitution degree of acetyl group in acetylhyaluronate generated thereby. Under the same condition as the above-mentioned Manufacturing Example 1, the relationship between the reaction catalyst amount and the intrinsic viscosity (FIG. 3) and that between the reaction catalyst amount and the substitution degree of acetyl group (FIG. 4) were studied when the mount of sulfuric acid was changed.

As can be seen from these charts, while the degree of acetyl group substitution increases as the amount of sulfuric acid increases, the viscosity decreases substantially in proportion thereto.

With respect to thus obtained acetylhyaluronate, the following usefulness tests were conducted. Namely, thread-forming ability test, moisture evaporation test, and skin-softening effect measurement test were respectively conducted concerning its usability, moisturizing effect, and skin-softening effect.

Thread-Forming Ability Test

In a thermo-hygrostat (at a temperature of 25° C. and a relative humidity of 50%), 1 cm of a glass rod having a diameter of about 7 mm was immersed in a sample solution with a concentration of 2% contained in a glass beaker having a capacity of 100 ml. Then, the thread length obtained when the beaker was descended at a velocity of 5 cm/min was measured.

Water Evaporation Test

It was based on occlusion effect (moisture nonvolatility) measurement test method.

Into filter paper (No. 2), 0.5 ml of a sample solution having a concentration of 1% was uniformly infiltrated and dried overnight under reduced pressure at room temperature. Then, this filter paper was attached to an opening portion of a plastic Petri dish containing 5 ml of water and, in a thermo-hygrostat (at a temperature of 25° C. and a relative humidity of 50%), its change in weight was measured over time. When being left for a certain time, the weight of the sample solution decreased in proportion to time. Accordingly, the weight of the test sample was plotted with reference to the time passed since it had been left. The gradient of its approximate line was defined as constant of water evaporating rate k (mg/min), from which the occlusion effect was evaluated. Namely, the occlusion effect is higher as the value of k is smaller.

Skin-Softening Test

It was based on stratum corneum softening effect test method.

A keratin layer collected from the back of a guinea pig by a heating and trypsin treatment process was cut into a slice of 2×30 mm. It was set in a continuous dynamic viscoelasticity measurement apparatus (manufactured by Toyo Seiki Co., Ltd and Shiseido Co., Ltd) and its elastic modulus was measured three times at every three minutes over time. The avenge thereof was defined as the measured value of the elastic modulus before applying the sample solution. Then, 2 μl of the sample solution was applied to the keratin layer and spread thereon with a width of 3 to 4 mm. The measurement was similarly conducted for a period of two hours. Then, the stratum corneum softening effect was evaluated in terms of the ratio of the elastic modulus after the application to that before the application. Namely, the stratum corneum softening effect is higher as the ratio of elastic modulus is smaller.

Thread-Forming Ability Pretest

Thread-forming ability test was conducted as mentioned above with respect to the following sample solutions:

Sample solution 1: 0.2% aqueous solution of sodium hyaluronate (HA) having a molecular weight of 1,200,000;

Sample solution 2: 0.2% aqueous solution of low molecular weight sodium acetylhyaluronate having a intrinsic viscosity of 170 cm$^3$/g and a substitution degree of acetyl group of 2.7;

Sample solution 3: 0.2% aqueous solution of low molecular weight sodium acetylhyaluronate having a intrinsic viscosity of 160 cm$^3$/g and a substitution degree of acetyl group of 2.8;

Sample solution 4: 0.2% aqueous solution of low molecular weight sodium acetylhyaluronate having a intrinsic viscosity of 140 cm$^3$/g and a substitution degree of acetyl group of 2.9;

Sample solution 5: 0.2% aqueous solution of low molecular weight sodium acetylhyaluronate having a intrinsic viscosity of 120 cm$^3$/g and a substitution degree of acetyl group of 3.0;

Sample solution 6: 0.2% aqueous solution of low molecular weight sodium acetylhyaluronate having a intrinsic viscosity of 110 cm$^3$/g and a substitution degree of acetyl group of 3.1; and Sample solution 7: 0.2% aqueous solution of low molecular weight sodium acetylhyaluronate having a intrinsic viscosity of 100 cm$^3$/g and a substitution degree of acetyl group of 3.2.

Figure 5:
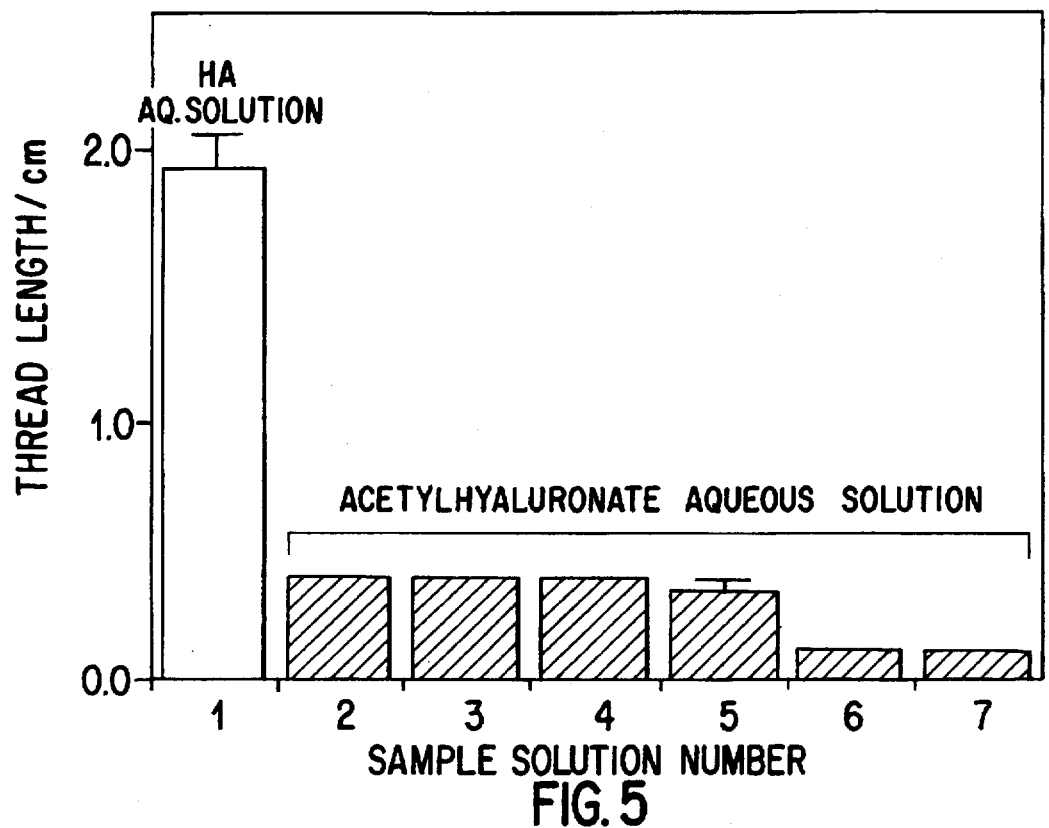
FIG. 5 is an explanatory chart showing the thread length in acetylhyaluronatein accordance with the present invention.

The results thereof are shown in FIG. 5.

As shown m this chart, the aqueous sodium hyaluronate solution has a thread length of about 2.0 cm. On the other hand, each of the aqueous sodium acetylated hyaluronate solutions has a thread length within about 0.1 to 0.4 cm which is significantly shorter than that in the aqueous sodium hyaluronate solution. In view of these results, it can be seen that the thread-forming ability has been clearly improved.

Based on these results, it has been decided that the thread-forming ability would be evaluated by the thread length.

Water Evaporation Measurement Pretest

Occlusion effect measurement test was conducted as mentioned above with respect to the following sample solutions:

Sample solution 1: ion-exchanged water;

Sample solution 2: 0.2% aqueous solution of tow molecular weight sodium acetylhyaluronate having a intrinsic viscosity of 200 cm$^3$/g and a substitution degree of acetyl group of 2.6;

Sample solution 3: 02% aqueous solution of low molecular weight sodium acetylhyaluronate having a intrinsic viscosity of 170 cm$^3$/g and a substitution degree of acetyl group of 2.7;

Sample solution 4: 0.2% aqueous solution of low molecular weight sodium acetylhyaluronate having a intrinsic viscosity of 160 cm$^3$/g and a substitution degree of acetyl group of 2.8;

Sample solution 5: 0.2% aqueous solution of low molecular weight sodium acetylhyaluronate having a intrinsic viscosity of 120 cm$^3$/g and a substitution degree of acetyl group of 3.0;

Sample solution 6: 0.2% aqueous solution of low molecular weight sodium acetylhyaluronate having a intrinsic viscosity of 100 cm$^3$/g and a substitution degree of acetyl group of 3.2;

Sample solution 7: 0.2% aqueous solution of low molecular weight sodium acetylhyaluronate having a intrinsic viscosity of 90 cm$^3$/g and a substitution degree of acetyl group of 3.4;

Sample solution 8: 0.2% aqueous solution of sodium hyaluronate (HA) having a molecular weight of 900,000; and Sample solution 9: 1% aqueous solution of propylene glycol (PG).

Figure 6:
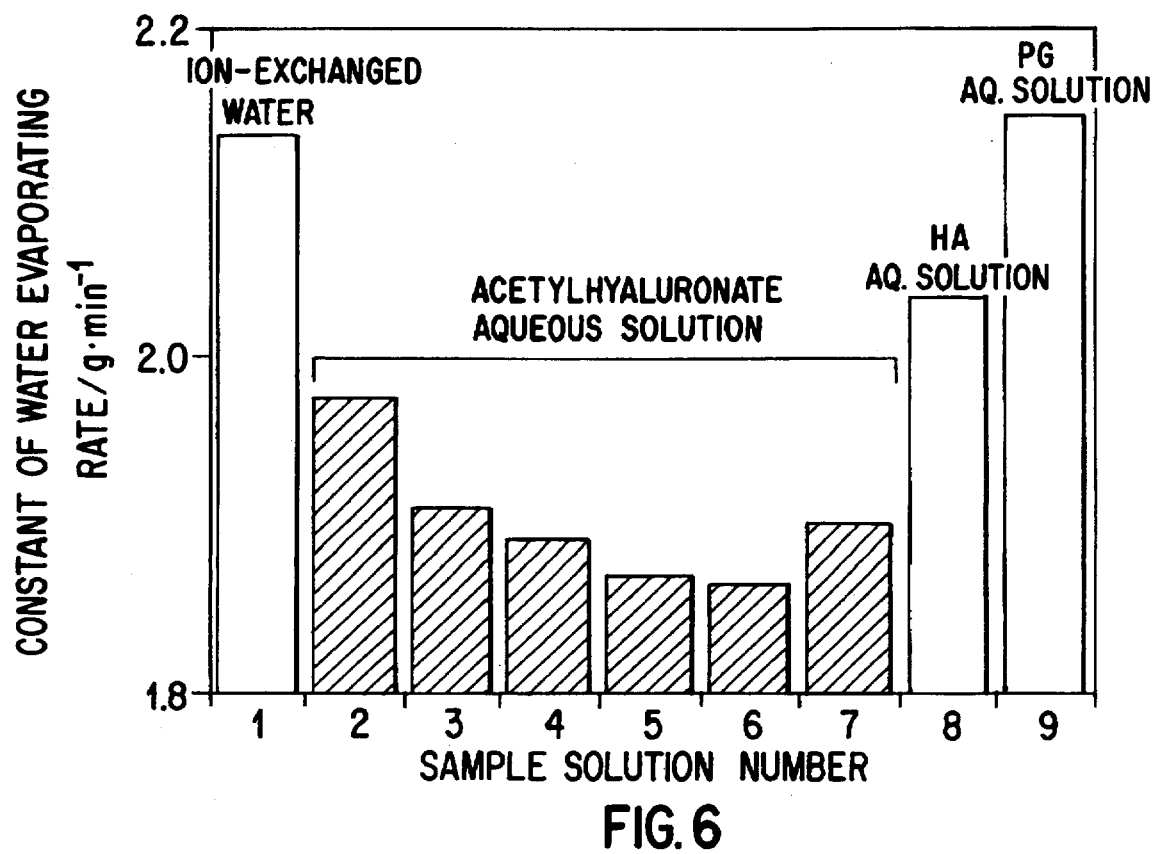
FIG. 6 is an explanatory chart showing the water evaporating rate in acetylhyaluronate in accordance with the present invention.

The results thereof is shown in FIG. 6.

As can be seen from this chart, as compared with ion-exchanged water, moisturizing effect is high when sodium hyaluronate or propylene glycol, which is a typical humectant, is added; while sodium acetylhyaluronate has a moisturizing effect which is further superior to that of sodium hyaluronate or propylene glycol.

Skin-Softening Effect Pretest

Skin-softening effect measurement test was conducted as mentioned above with respect to the following sample solutions:

Sample solution 1: ion-exchanged water;

Sample solution 2: 0.2% aqueous solution of low molecular weight sodium acetylhyaluronate having a intrinsic viscosity of 120 cm$^3$/g and a substitution degree of acetyl group of 3.0;

Sample solution 3: 0.2% aqueous solution of low molecular weight sodium acetylhyaluronate having a intrinsic viscosity of 110 cm$^3$/g and a substitution degree of acetyl group of 3.1;

Sample solution 4: 0.2% aqueous solution of low molecular weight sodium acetylhyaluronate having a intrinsic viscosity of 100 cm$^3$/g and a substitution degree of acetyl group of 3.2;

Sample solution 5: 0.2% aqueous solution of sodium hyaluronate (HA) having a molecular weight of 900,000; and Sample solution 6: 5% aqueous solution of glycerine (DG).

Figure 7:
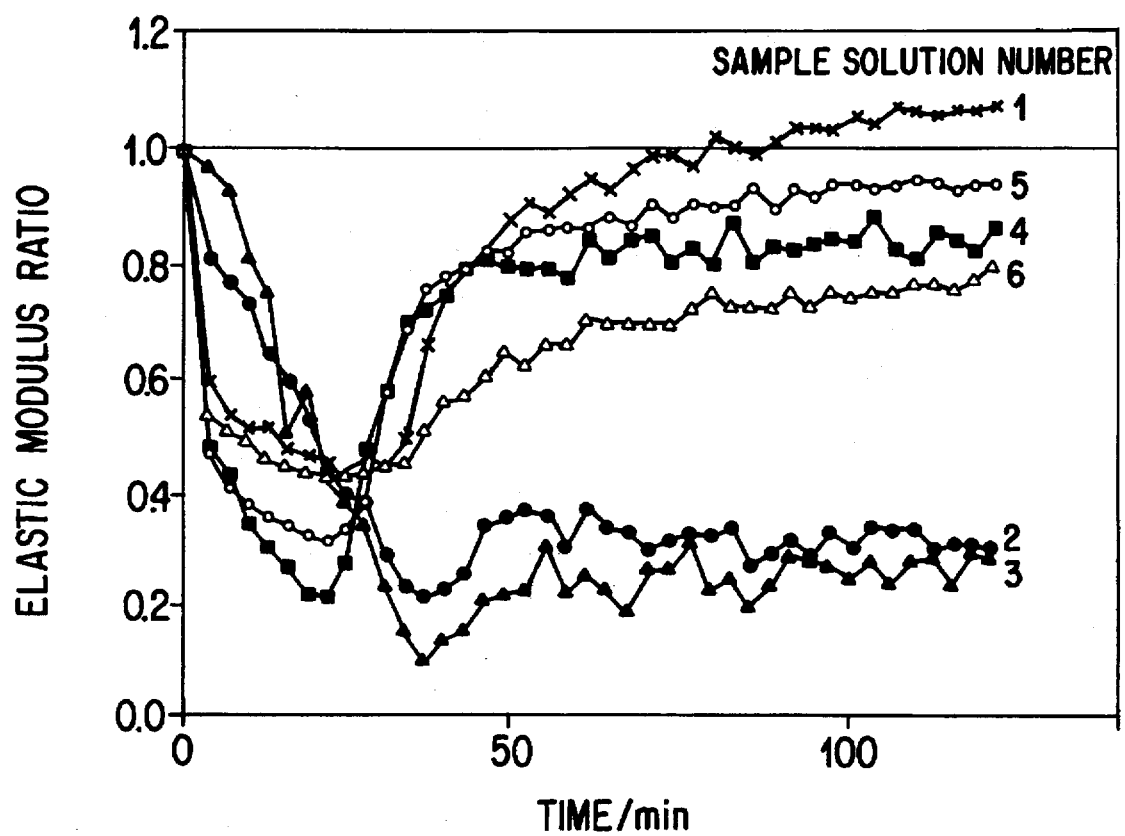
FIG. 7 is an explanatory chart showing the stratum corneum softening effect of acetylhyaluronate in accordance with the present invention.

The results thereof are shown in FIG. 7.

As can be seen from this chart, in the section to which ion-exchanged water has been applied, until 20 minutes after the application, the elastic modulus ratio decreases due to the moisture infiltrating into the keratin layer, thereby increasing the softness of the keratin layer. Then, about 30 minutes after the application, due to being elastic resulting from water evaporation, the elastic modulus ratio returns to the value before the application and, due to the rebound in water evaporation, further to a value slightly exceeding 1. In the section to which aqueous sodium hyaluronate has been applied, the recovered value of softness is slightly lower than that in the section where ion-exchanged water has been applied and there is a slight effect. It is, however, recovered to about 0.9 in about 50 minutes, thereby being understood that thre is a low stratum corneum softening effect. By contrast, unlike the sections where ion-exchanged water and hyaluronic acid have been applied, the section to which the aqueous glycerine solution has been applied maintains the value of about 0.7, thereby yielding a relatively high softness maintaining effect.

On the other hand, in the section to which low molecular weight sodium acetylhyaluronate has been applied, the elastic modulus ratio is maintained at about 0.3 even 120 minutes after the application, thereby yielding a very high stratum corneum softening effect.

Based on these test results, it has been decided that the skin-softening effect would be evaluated by the average value of the elastic modulus ratio at least 60 minutes after the application in view of the softness maintaining effect in the keratin layer.

As can be seen from the foregoing pretests, it is understood that acetylhyaluronate is much superior to hyaluronic acid or the like in terms of thread-forming ability, moisturizing effect, and skin-softening effect, for example.

Next, each parameters in the above-mentioned method of manufacturing acetylhyaluronate was changed so as to prepare various kinds of acetylhyaluronate having various intrinsic viscosity (molecular weight) values and numbers of acetyl group substitution, by which the above-mentioned effects were inspected.

The results thereof will be shown in the following.

First, in Table 1, various kinds of acetylhyaluronate having respective substitution degrees of acetyl group were prepared with a intrinsic viscosity of about 120 cm$^3$/g to inspect various effects mentioned above. The results thereof are shown in Table 1.

TABLE 1

|  | HA | AcHA | | | | | |
|---|---|---|---|---|---|---|---|
| Intrinsic viscosity (cm$^3$/g) | 1400 | 125 | 122 | 120 | 118 | 115 | 113 |
| Substitution degree of acetyl group | 0 | 2.6 | 2.8 | 3.0 | 3.2 | 3.4 | 3.6 |
| Thread length (cm) | 2.00 | 0.45 | 0.40 | 0.34 | 0.32 | 0.31 | 0.30 |
| Constant of water evaporation rate (g/min) | 2.03 | 2.01 | 1.91 | 1.87 | 1,87 | 1.90 | 2.00 |
| Elastic modulus ratio | 0.92 | 0.89 | 0.61 | 0.32 | 0.26 | 0.54 | 0.87 |

As clearly from Table 1, in cases where the intrinsic viscosity is about 120 cm$^3$/g, there was remarkable improvement in thread-forming ability, skin-softening effect, and moisturizing effect when the substitution degree of acetyl group is 2.6 or more. However, when the substitution degree of acetyl group was 3.6, moisturizing effect and skin-softening effect tend to decrease so as to be difficult it to be used for an external preparation for skin.

Next, the inventors prepared various kinds of acetylhyaluronate having respective intrinsic viscosity values with a substitution degree of acetyl group at about 3.0 and inspected their effects.

TABLE 2

|  | HA | AcHA | | | | | |
|---|---|---|---|---|---|---|---|
| Intrinsic viscosity (cm$^3$g/) | 1400 | 200 | 160 | 120 | 100 | 80 | 50 |
| Substitution degree of acetyl group | 0 | 2.8 | 2.9 | 3.0 | 3.1 | 3.0 | 3.1 |
| Thread length (cm) | 2.00 | 1.03 | 0.61 | 0.34 | 0.21 | 0.10 | 0.08 |
| Constant of water evaporation rate (g/min) | 2.03 | 1.99 | 1.89 | 1.87 | 1.85 | 1.94 | 2.01 |
| Elastic modulus ratio | 0.92 | 0.80 | 0.57 | 0.32 | 035 | 0.61 | 0.79 |

The above results indicate that, in cases where the substitution degree of acetyl group is about 3.0, when the intrinsic viscosity exceeds 200 cm$^3$/g, improvement in thread-forming ability becomes insufficient even by acetylation. On the other hand, when the intrinsic viscosity is less than 50 cm$^3$/g, moisturizing effect and skin-softening effect, for example, tend to become insufficient.

In the following, more specific examples of the cosmetic preparation in accordance with the present invention will be explained.

| | |
|---|---|
| (1) Dipropylene glycol | 5.0 |
| (2) Glycerine | 8.0 |
| (3) Carboxyvinylpolymer | 0.1 |
| (4) Triethanolamine | 1.0 |
| (5) Stearic acid | 2.0 |
| (6) Sorbitan monooleate | 2.0 |
| (7) Stearyl alcohol | 1.5 |
| (8) Vaseline | 4.0 |
| (9) Squalane | 5.0 |
| (10) Glycerol tri-2-ethylhexanoate | 2.0 |
| (11) Ethyl paraben | 0.2 |
| (12) Perfume | 0.05 |
| (13) Acetylhyaluronate | 0.1 |
| (intrinsic viscosity: 102 cm$^3$/g, substitution degree of acetyl group: 3.2) | |
| (14) Ion-exchanged water | 47.05 |

A milky lotion was prepared by the conventional method. It was favorable in terms of affinity and wetness according to a panel evaluation.

EXAMPLE 2

Moisturizing Cream

| | |
|---|---|
| (1) 1,3-Butyleneglycol | 9.5 |
| (2) Acetylhyaluronate | 0.5 |
| (intrinsic viscosity: 72 cm$^3$/g, substitution degree of acetyl group: 3.0) | |
| (3) POE(25) cetyl alcohol ether | 3.0 |
| (4) Glycerine monostearate | 2.0 |
| (5) Cetyl alcohol | 3.0 |
| (6) Solid paraffin | 2.0 |
| (7) Vaseline | 5.0 |
| (8) Squalane | 15.0 |
| (9) Butyl paraben | 0.2 |
| (10) Chondroitin | 0.05 |
| (11) Perfume | 0.1 |
| (12) Ion-exchanged water | 59.65 |

A moisturizing cream was prepared by the conventional method. It was favorable in terms of affinity and wetness according to a panel evaluation.

EXAMPLE 3

Massage Cream

| | |
|---|---|
| (1) Acetylhyaluronate | 1.0 |
| (intrinsic viscosity: 180 cm$^3$/g substitution degree of acetyl group: 3.1) | |
| (2) POE(20) sorbitan monwmte | 2.0 |
| (3) Glycerine monostearate | 2.5 |
| (4) Stearic acid | |
| (5) Potassium hydroxide | 0.1 |
| (6) Cetyl alcohol | 3.0 |
| (7) Solid paraffin | 5.0 |
| (8) Vaseline | 10.0 |
| (9) Liquid parraffin | 35.0 |
| (10) Isopropyl myristate | 10.0 |
| (11) Butyl paraben | 0.2 |
| (12) Alanine | 0.05 |
| (13) Perfume | 0.1 |
| (14) Ion-exchanged water | 29.05 |

A massage cream was prepared by the conventional method. It was favorable in terms of affinity and wetness according to a panel evaluation.

EXAMPLE 4

Cleansing Cream

| | |
|---|---|
| (1) Stearic acid | 12.0 |
| (2) Myristic acid | 14.0 |
| (3) Lauric acid | 5.0 |
| (4) Jojoba oil | 3.0 |
| (5) Potassium hydroxide | 5.0 |
| (6) Sorbitol (70% aqueous sorbitol solution) | 20.0 |
| (7) Acetylhyaluronate | 2.0 |
| (intrinsic viscosity: 148 cm$^3$/g, substitution degree of acetyl group: 3.4) | |
| (8) 1,3-Butyleneglycol | 13.0 |
| (9) POE(20) glycerol monostearate | 2.0 |
| (10) Acylmethyltaurine | 4.0 |
| (11) Glycine | 0.01 |
| (12) Chelating agent | appropriate amount |
| (13) Perfume | appropriate amount |
| (14) Ion-exchanged water | 20.0 |

<Method of Preparation>

Ingredients (1) to (4), (6) to (8), and (11) were dissolved by heating and the mixture was maintained at 70° C. Ingredient (5) was dissolved in ingredient (14) and the above-mentioned mixture was added thereto while being stirred. After a sufficient neutralization reaction, ingredients (9) and (10) were added thereto and then ingredients (12) and (13) were added thereto. After deaeration and cooling, a cleansing foam was obtained.

It was favorable in terms of affinity and wetness according to a panel evaluation.

EXAMPLE 5

Hair Tonic

| | |
|---|---|
| (1) Ethanol | 75.0 |
| (2) Ion-exchanged water | 23.2 |
| (3) Percutaneous absorption accelerator | appropriate amount |
| (4) Solubilizer | appropriate amount |
| (5) pH adjustor | appropriate amount |
| (6) Perfume | appropriate amount |
| (7) Acetylhyaluronate | 0.1 |
| (intrinsic viscosity: 120 cm$^3$/g, substitution degree of acetyl group: 3.0) | |

A hair tonic was prepared by the conventional method. It yielded no sliminess, a favorable affinity, and a refreshing feel of use according to a panel evaluation.

EXAMPLE 6

Softening Lotion

| | |
|---|---|
| (1) Ion-exchanged water | 90.2 |
| (2) Acetylhyaluronate | 0.1 |
| (intrinsic viscosity: 120 cm$^3$/g, substitution degree of acetyl group: 3.0) | |
| (3) 1,3-Butyleneglycol | 5.0 |
| (4) Glycerine | 4.0 |
| (5) Antiseptic | appropriate amount |

A softening lotion was prepared by the conventional method. It yielded no sliminess, a favorable affinity, and a refreshing feel of use according to a panel evaluation.

As explained in the foregoing, since low molecular weight acetylhyaluronate in accordance with the present invention has a specific molecular weight and substitution degree of acetyl group, it can exhibit excellent skin-softening effect and moisturizing effect, while appropriately suppressing the thread-forming ability inherent in hyaluronic acid.

We claim:

1. Acetylhyaluronate having the following characteristics:
   intrinsic viscosity: 50 to 200 cm$^3$/g
   substitution degree of acetyl group: 2.6 to 3.6 (excluding N-acetyl group).

2. A skin-softening composition mainly composed of acetylhyaluronate according to claim 1.

3. A method of manufacturing acetylhyaluronate comprising the steps of suspending hyaluronic acid powder in an acetic anhydride solvent and then adding concentrated sulfuric acid thereto to effect acetylation.

4. A method of manufacturing acetylhyaluronate according to claim 3, wherein acetic acid is mixed into the acetic anhydride solvent with a mixing ratio of acetic acid:acetic anhydride at 1:4 to 1:1.

5. A method of manufacturing acetylhyaluronate according to claim 3, wherein acetic acid is mixed into the acetic anhydride solvent with a mixing ratio of acetic acid:acetic anhydride at 2:1 to 4:1.

6. A method according to claim 3, wherein an amount of concentrated sulfuric acid added is 2 to 7% by volume with respect to the solvent.

7. A method of purifying acetylhyaluronate comprising the steps of adding raw acetylhyaluronate to an aqueous acetone solution, adding and dissolving sodium lactate therein, and then adding acetone thereto to precipitate and obtain said purified acetylhyaluronate.

8. A method according to claim 7, wherein an amount of sodium lactate added is 1 to 3% by weight with respect to the aqueous acetone solution.

9. A method of purifying acetylhyaluronate, wherein the method according to claim 7 is applied to raw acetylhyaluronate obtained by a method of manufacturing comprising the steps of suspending hyaluronic acid powder in an acetic anhydride solvent and then adding concentrated sulfuric acid thereto to effect acetylation.

* * * * *